United States Patent [19]
Beane et al.

[11] Patent Number: 5,906,577
[45] Date of Patent: May 25, 1999

[54] DEVICE, SURGICAL ACCESS PORT, AND METHOD OF RETRACTING AN INCISION INTO AN OPENING AND PROVIDING A CHANNEL THROUGH THE INCISION

[75] Inventors: Richard Beane, Hingham; Steve Ek, Bolton; Allison C. Niemann, Brighton, all of Mass.; Maureen E. Carroll, Atlanta, Ga.; Randall J. Hasslinger, Alpharetta, Ga.; Edward I. Stamm, Jr., Atlanta, Ga.; Javier Verdura, Marietta, Ga.

[73] Assignees: University of Massachusetts, Boston, Mass.; Smith & Nephew, Inc., Andover, Mass.

[21] Appl. No.: 08/847,155

[22] Filed: Apr. 30, 1997

[51] Int. Cl.⁶ .................................................. A61B 17/00
[52] U.S. Cl. ......................... 600/207; 600/208; 600/206; 600/245
[58] Field of Search .................................... 600/201, 207, 600/208, 235, 245; 128/850, 852, 856, 887; 606/213

[56] References Cited

U.S. PATENT DOCUMENTS

| | | | |
|---|---|---|---|
| 3,244,169 | 4/1966 | Baxter | 128/850 X |
| 5,159,921 | 11/1992 | Hoover | 600/207 |
| 5,299,582 | 4/1994 | Potts | 128/846 |
| 5,336,193 | 8/1994 | Rom et al. | 604/171 |
| 5,366,478 | 11/1994 | Brinkerhoff et al. | 606/213 |
| 5,437,683 | 8/1995 | Neumann et al. | 606/151 |
| 5,480,410 | 1/1996 | Cushieri et al. | 606/213 |
| 5,514,133 | 5/1996 | Golub et al. | 606/1 |
| 5,522,791 | 6/1996 | Leyva | 600/207 |
| 5,524,644 | 6/1996 | Crook | 128/888 |
| 5,526,536 | 6/1996 | Cartmill | 2/161.7 |
| 5,634,937 | 6/1997 | Mollenauer et al. | 606/213 |
| 5,636,645 | 6/1997 | Ou | 128/898 |
| 5,640,977 | 6/1997 | Leahy et al. | 128/897 |
| 5,672,168 | 9/1997 | De La Torre et al. | 606/1 |
| 5,741,298 | 4/1998 | MacLeod | 606/213 |
| 5,813,409 | 9/1998 | Leahy et al. | 128/897 |

FOREIGN PATENT DOCUMENTS

| | | | |
|---|---|---|---|
| 1748800 | 7/1992 | U.S.S.R. | 600/208 |
| 2 071 502 | 9/1981 | United Kingdom. | |
| WO 95/07056 | 3/1995 | WIPO. | |
| WO 95/22289 | 8/1995 | WIPO. | |
| WO 95/27445 | 10/1995 | WIPO. | |
| WO 95/27468 | 10/1995 | WIPO. | |
| WO 96/10963 | 4/1996 | WIPO. | |
| WO 97/11642 | 4/1997 | WIPO. | |

*Primary Examiner*—Jeffrey A. Smith
*Attorney, Agent, or Firm*—Fish & Richardson P.C.

[57] ABSTRACT

A device for retracting edges of an incision in a surface to form an opening including: a flexible, tubular skirt having an upper end, a lower end, and a channel therebetween; a ring connected to the lower end of the skirt for maintaining the lower end in an open configuration and defining an exit opening to the channel; and an inflatable collar connected to the skirt and surrounding the upper end. The ring is designed to fit through the incision and remain under the surface when it is oriented parallel to surface. The collar, when inflated, maintains the upper end in an open configuration and defines an entry opening to the channel. During use, the ring is inserted through the incision and the collar is inflated while remaining outside of the incision, thereby drawing the skirt against the edges of the incision and retracting the edges of the incision to form the opening. The retracting device can be included in a surgical access port, which further includes a flexible sleeve connected to at least one of the inflatable collar and the skirt, extending the channel from the exit opening of the skirt to an open end of the flexible sleeve distal to the skirt. The device can include a light source in the vicinity of the exit opening.

43 Claims, 14 Drawing Sheets

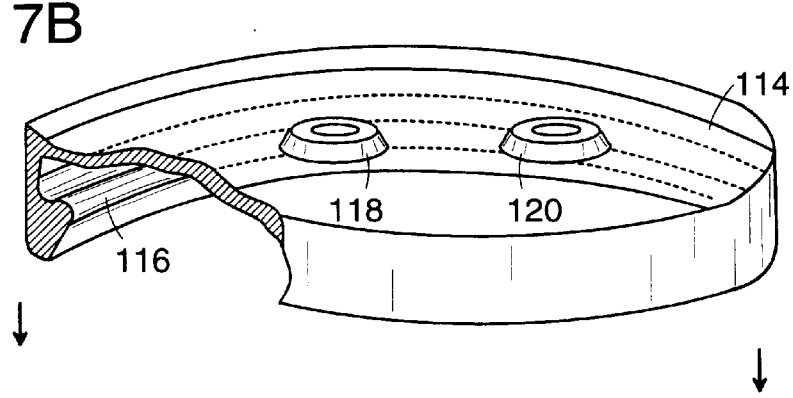
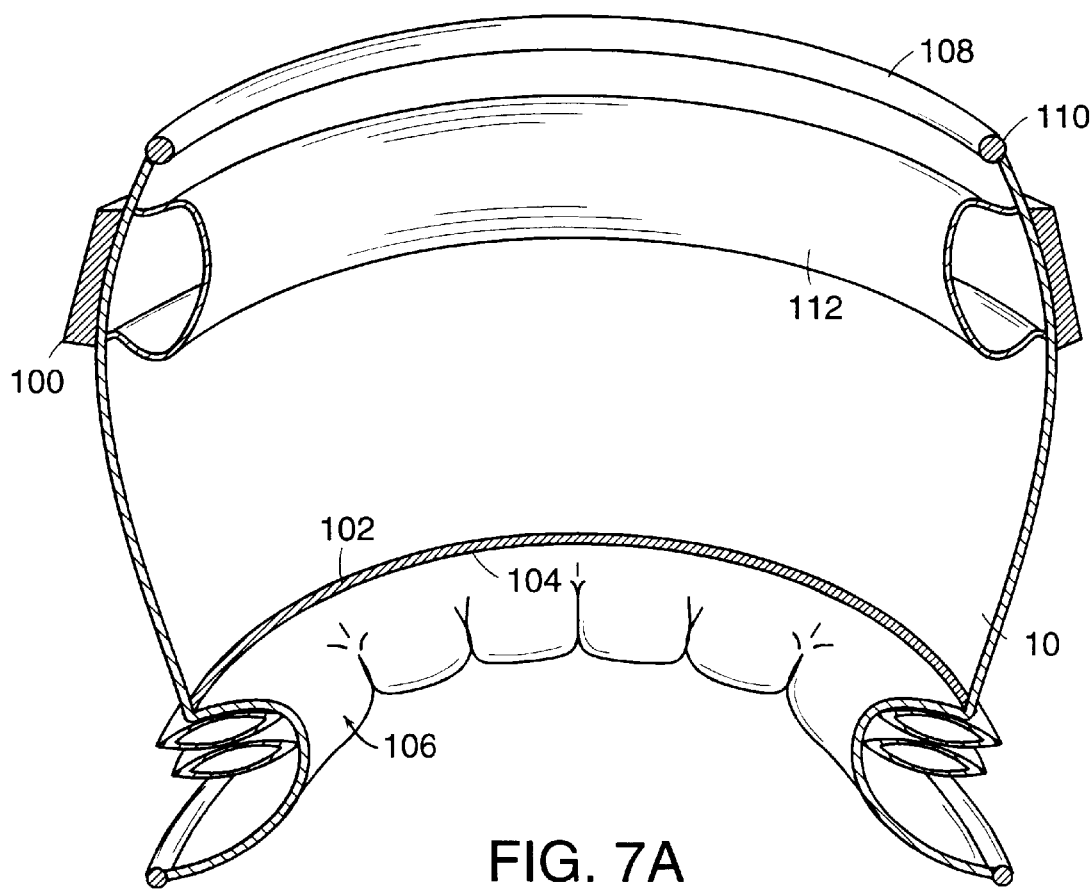

DEVICE, SURGICAL ACCESS PORT, AND METHOD OF RETRACTING AN INCISION INTO AN OPENING AND PROVIDING A CHANNEL THROUGH THE INCISION

BACKGROUND OF THE INVENTION

This invention relates to the field of surgical devices. More particularly, the invention relates to a surgical access port, which provides a gas-tight seal for a hand or instrument to be inserted through the opening into a patient's body cavity.

Abdominal surgery typically involves an incision in the abdominal wall large enough to accommodate a surgeon's hands, multiple instruments, and illumination of the body cavity. While large incisions simplify access to the body cavity during a surgery, they also increase trauma, require extended recovery time, and can result in unsightly scars. In response to these drawbacks, minimally invasive surgical methods have been developed.

In minimally invasive abdominal surgery, several smaller incision are made into the abdominal wall. One of the openings is use to inflate the abdominal cavity with gas, which lifts the abdominal wall away from underlying organs and provides space to perform the desired surgery. This process is referred to as insufflation of the body cavity. Additional openings can be used to accommodate instruments for illuminating and viewing the cavity, as well as instruments involved in actually performing the surgery, e.g., instruments to manipulate, cut, or resect organs and tissue. While minimally invasive surgical methods overcome certain drawbacks of traditional methods, there are still various disadvantages. In particular, there is limited tactile feedback from the manipulated tissue to the surgeon hands. Also, tissue that is to be removed from the body cavity must be removed in pieces that are small enough to fit through one of the incisions.

Recently, new surgical methods have been developed that combine the advantages of the traditional and minimally invasive methods. In these new methods, small incisions are still used to inflate, illuminate, and view the body cavity, but in addition, an intermediate incision is made into the abdominal wall to accommodate the surgeon's hand. The intermediate incision must be properly retracted to provide a suitable-sized opening, and the perimeter of the opening is typically protected with a surgical drape to prevent bacterial infection. A sealing mechanism is also required to prevent the loss of insufflation gases while the surgeon's hand is either inserted into or removed from the body cavity though the retracted incision.

SUMMARY OF THE INVENTION

The invention features a surgical access port that allows a surgeon's hand or instrument to access a patient's body cavity through a sealed opening. The access port includes two parts, a wound retractor and a sealing sleeve. The wound retractor is designed to retract the edges of an incision made into a body cavity into an opening, and to seal around the edges of the opening, thereby forming a gas-tight connection between the body cavity and the interior of the access port. The sealing sleeve connects to the wound retractor external to the body cavity and provides a path for a surgeon to insert his hand through the opening formed by the wound retractor. The sealing sleeve seals around a surgeon's arm or a surgeon's glove, when the surgeon's hand is inserted into the body cavity, and seals the opening when the surgeon's hand is removed from the access port. Thus, the port provides hand access to the body cavity, and prevents gases in the body cavity, such as insufflation gases, from escaping into the surroundings.

In general, in one aspect, the invention features a device for retracting edges of an incision in a surface to form an opening. The device includes: a flexible, tubular skirt having an upper end, a lower end, and a channel therebetween; a ring connected to the lower end of the skirt for maintaining the lower end in an open configuration and defining an exit opening to the channel; and an inflatable collar connected to the skirt and surrounding the upper end. The ring is designed to fit through the incision and remain under the surface when it is oriented parallel to the surface. The collar, when inflated, maintains the upper end in an open configuration and defines an entry opening to the channel. During use, the ring is inserted through the incision and the collar is inflated while remaining outside of the incision, thereby drawing the skirt against the edges of the incision and retracting the edges of the incision to form the opening.

The retracting device can include the following features. The collar when fully inflated has an inner aperture having a diameter greater than the length of the incision. The device can also include a light source, such as an optic fiber or fiber optic cable, connected to the lower end of the skirt. The skirt can include a hem-shaped pocket that encloses the ring. The ring can be formed by filling a pocket with at least one of a gas and a liquid. The ring can have a substantially elliptical shape. The device can also include a second ring adjacent to an outer perimeter of the inflatable collar for reinforcing the entry opening, as well as a detachable cap, adapted to be received by the second ring, for sealing the entry opening. Furthermore, the device can include an inflatable cuff connected to an inner wall of the skirt and surrounding the entry opening for sealing around a surgeon's arm inserted into the channel, as well as a detachable plug, adapted to be received by the inflatable cuff, for covering the entry opening.

The retracting device can be included in a surgical access port, which further includes a flexible sleeve connected to at least one of the inflatable collar and the skirt, extending the channel from the exit opening of the skirt to an open end of the flexible sleeve distal to the skirt. In some embodiments, the flexible sleeve can be removed and reattached to the device, or it can be permanently affixed. The access port can include a light source connected to the skirt in the vicinity of the exit opening, and the flexible sleeve can include an iris valve.

In one embodiment of the access port, the flexible sleeve includes an inner sleeve and an outer sleeve forming a chamber therebetween, and an inlet port for inflating the chamber, whereby inflating the chamber compresses together a central portion of the inner sleeve, thereby sealing the channel. A pair of drawstrings can be attached to opposite sides of the central portion of the inner sleeve and pull the sides in opposite directions toward the outer sleeve, thereby collapsing the central portion of the inner sleeve into two flattened portions contacting each other to form a seal. Furthermore, the central portion of the inner sleeve can include two sealed regions opposite one another in which immediately adjacent portions of the inner sleeve are welded together, thereby dividing the central portion into two substantially flattened portions extending along the length of the channel adjacent to one another.

In another embodiment, the access port includes a flap valve that connects to the open end of the flexible sleeve and extends into the channel. The flap valve seals the channel when there is a positive pressure differential between the channel and the surroundings. A pair of drawstrings can be attached to opposite ends of the flap valve and pull the ends in opposite directions to enhance the sealing ability of the flap valve.

In a further embodiment, the access port includes an inflatable cuff attached to an inner surface of the sleeve for sealing around a surgeon's arm. The inflatable cuff can be surrounded by a backing of a substantially non-expandable material. Furthermore, a second ring can be connected to the sleeve and surround the open end of the sleeve. To seal the open end, a detachable cap adapted to be received by the second ring can be used.

In another embodiment, the access port can include a sealing collar attached to the sleeve and surrounding the open end, and a glove having a flange at the open end of the glove. The sealing collar can have a groove along its inner perimeter that mates with or engages the flange and seals the channel when inserted into the groove.

In a related embodiment, the access port includes a sealing collar attached to the sleeve and surrounding the open end, and a glove having an enlarged cuff. The sealing collar including an inwardly expanding inflatable bladder that mates with the enlarged cuff and seals the opening when the glove is inserted into the sleeve.

In another related embodiment, the access port includes a sealing collar attached to the sleeve and surrounding the open end, a bracelet having a fixed diameter, and a surgical glove. The sealing collar has a groove along its inner perimeter that mates with the bracelet. During use, the bracelet is worn by a surgeon underneath the surgical glove and is mated to the sealing collar so that a portion of the glove is held within the groove by the bracelet, thereby sealing the channel.

In another aspect, the invention features a surgical access port, for use with a surgical glove, including a device for retracting the edges of a surgical incision to form an opening into a patient's body cavity, a sealing sleeve attached to the device external to the body cavity, and a semi-rigid bracelet having a fixed diameter. The sealing sleeve includes a flexible sleeve providing a channel from its open end distal to the retracting device through to the opening, and a sealing collar attached to the sleeve and surrounding the open end that mates with the bracelet. During use, the bracelet is worn by a surgeon underneath the surgical glove and is mated to the sealing collar, thereby fastening a portion of the glove to the sealing collar and sealing the channel. In some embodiments, the access port further includes the surgical glove.

The invention also features a method of using the new access ports. The steps include: placing the bracelet around an arm of the surgeon; placing the glove over a hand of the surgeon so that the glove extends over the bracelet; inserting the gloved hand into the access port; and attaching the portion of the inserted glove to the access port by mating the bracelet with the sealing collar of the access port.

In further aspects, the invention features a surgical access port including a device for retracting the edges of a surgical incision to form an opening into a patient's body cavity and a sealing sleeve attached to the device external to the body cavity. The sealing sleeve includes a flexible sleeve providing a channel from its open end distal to the retracting device through to the opening and a mechanism for sealing the channel. The mechanism includes drawstrings.

In one embodiment, the sealing sleeve further includes an outer sleeve surrounding the flexible sleeve and forming a chamber therebetween, and an inlet port for inflating the chamber. Inflating the chamber compresses together a central portion of the flexible sleeve, thereby sealing the channel. The drawstrings attach to opposite sides of the central portion of the flexible sleeve, pulling the sides in opposite directions toward the outer sleeve, thereby imparting a preferred flattened geometry to the central portion of the inner sleeve and enhancing the seal.

In another embodiment, the mechanism further includes a flap valve that connects to the open end of the flexible sleeve and extends into the channel. The flap valve seals the channel when there is a positive pressure differential between the channel and the surroundings. The drawstrings attach to opposite ends of the flap valve, pulling the ends in opposite directions, enhancing the sealing ability of the flap valve.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The invention has the following advantages.

Since the edges of the incision are retracted by simply inflating the collars, the wound retractor is easy to use. Furthermore, the wound retractor provides a seal around the perimeter of a retracted wound, from the inner abdominal wall to the surface of the skin. The seal prevents infection and provides a gas-tight connection between the body cavity and the remainder of the access port.

In the sealing sleeve portion of the access port, the flap valve and the inner sleeve, which is compressed by the inflatable chamber, provide a gas-tight seal around a surgeon's arm when the surgeon's hand is inserted into a patient's body cavity. This seal prevents insufflation gases from escaping. The effectiveness of this seal is improved by the drawstrings.

A light source connected to the base of the wound retractor can be used to illuminate the body cavity, making additional incisions for endoscopic illuminating means unnecessary.

Other features and advantages of the invention will be apparent from the following detailed description, and from the claims.

BRIEF DESCRIPTION OF THE DRAWING

FIGS. 7A and 7B are a cross-sectional views of another embodiment of a surgical access port.

DETAILED DESCRIPTION

The surgical access port is best described as having two parts, a wound retractor and a sealing sleeve.

The wound retractor includes a flexible tubular skirt having a first end reinforced with a stiff ring so that the first end is maintained in an open orientation, and a second end surrounded by one or more inflatable collars. The reinforced first end is inserted into the body cavity through an incision, providing a channel through the skirt from the outside to the inside of the body cavity. During use, the collars are inflated, thereby drawing out skirt within the incision and pulling the reinforced first end of the skirt tight against the inner wall of the patient's skin. As a result, the edges of the incision are retracted into an opening and the skirt seals around the perimeter of the opening along the inner abdominal wall to the outer surface of the skin.

A sealing sleeve is attached to the wound retractor portion above the inflatable collars. The sealing sleeve has an entry opening distal to the collars and extends the channel provided by the skirt. Within the sealing sleeve, a gas-tight seal is provided for conforming to the shape of an object (e.g., a hand or instrument) inserted through the channel into the body cavity.

Alternatively, the sealing sleeve can include means for attaching a surgeons glove to the entry opening of the sleeve. In these cases, the exterior of the glove seals the channel while a surgeon's hand can be inserted into the interior of the glove and access the body cavity.

Surgical Access Ports

Figure 1:
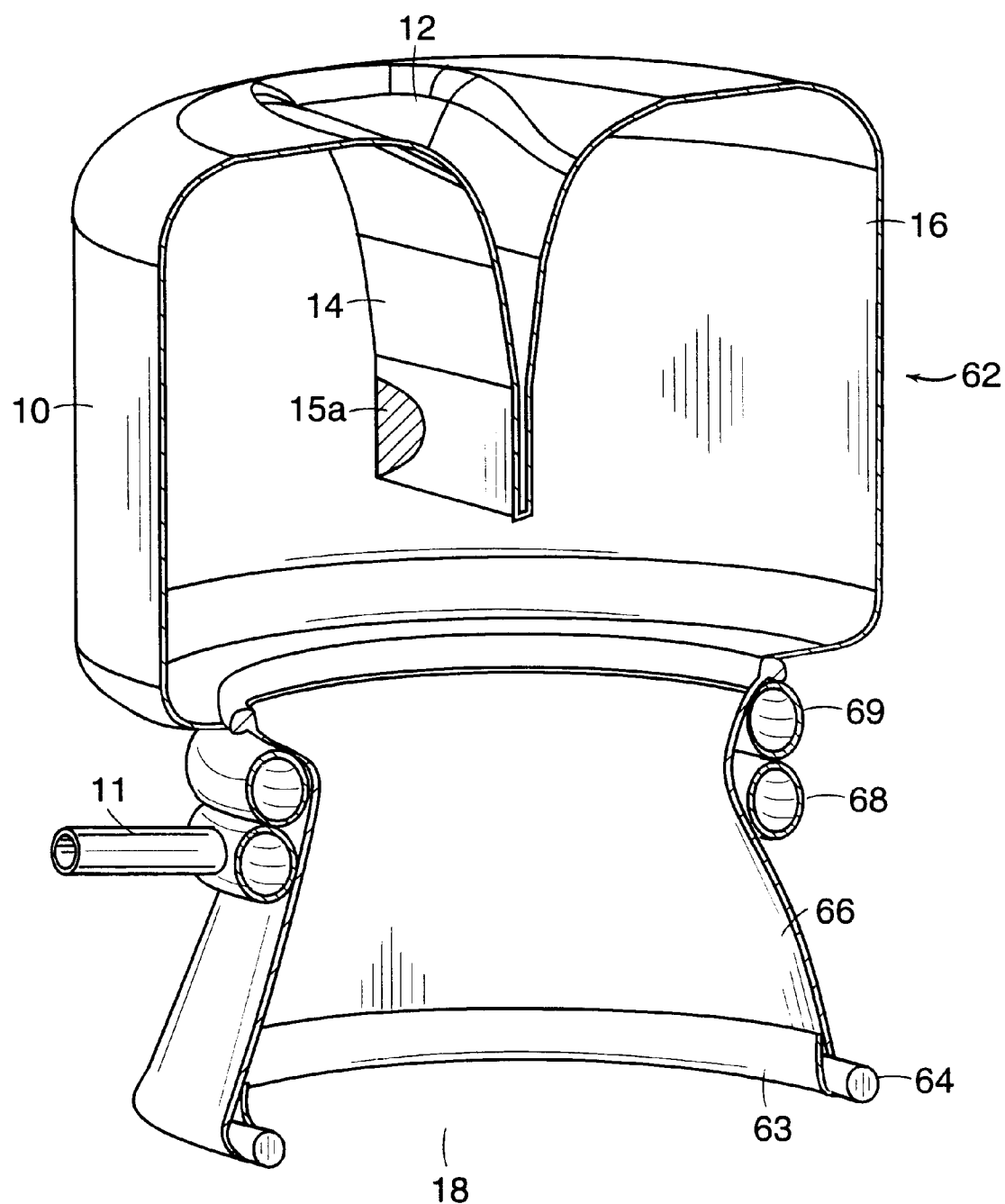
FIG. 1 is a cross-sectional view of a surgical access port.

As shown in FIG. 1, surgical access port 62 is a sleeve-like device having an entry opening 12 and an exit opening 18. During use, a surgeon inserts a hand into the entry opening 12 and accesses a patient's body cavity through exit opening 18, after the access port is inserted into the body cavity through an incision, and prevents gases used to insufflate the body cavity from escaping through the incision. A flexible skirt 66 surrounds exit opening 18 and has a hem-like pocket 63 at its end proximal to exit opening 18. Pocket 63 encloses a ring 64 so that the skirt and exit opening 18 are maintained in an open, substantially circular or elliptical orientation. Skirt 66 extends upward from exit opening 18 towards one or more inflatable collars 68 and 69 that surround skirt 66. The upper end of skirt 66 is connected to the upper-most collar 69, from the inner circumference of collar 69 to the top of collar 69. Each of the inflatable collars 68 and 69 respectively enclose an annular region. The annular regions may or may not be in fluid contact with one another, but they are isolated from the rest of the sleeve, body cavity, and surrounding. The collars 68 and 69 are inflated through one or more inlet ports 11. When collars 68 and 69 are in fluid communication with one another, only a single inlet port 11 is required.

An outer sleeve 10 is attached to the upper end of skirt 66 and extends upward towards entry opening 12. Outer sleeve 10 encloses an upper chamber 16, which is in fluid contact with gases from the body cavity when exit opening 18 is inserted through an incision into the body cavity. Outer sleeve 10 is inverted at the entry opening 12 forming a flap valve 14, which seals upper chamber 16 from the surroundings external to entry opening 12.

Figure 2A:
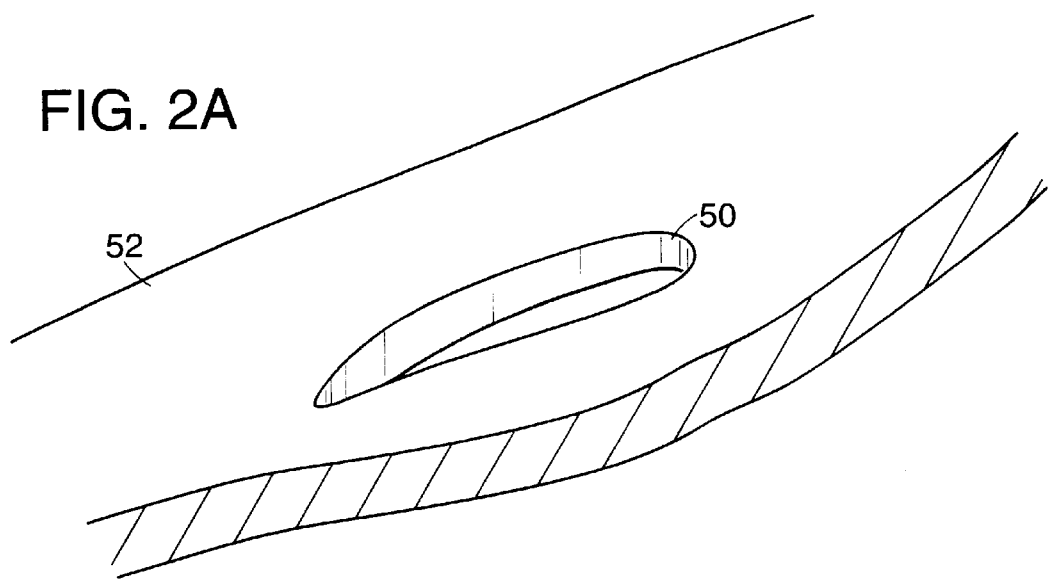
FIGS. 2A to 2E illustrate the steps in using the wound retractor portion of the access port of FIG. 1.
Figure 2B:
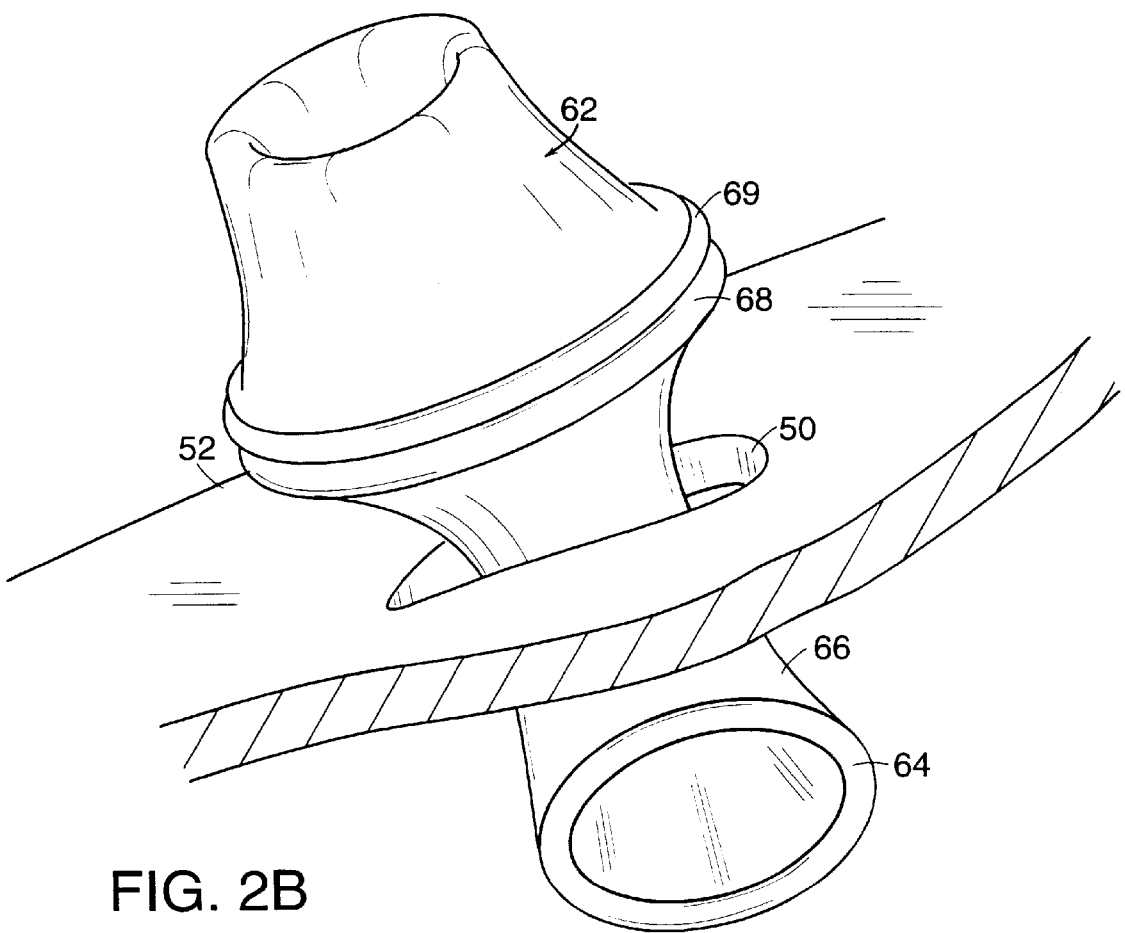

The lower portion of access port 62, which includes ring 64, skirt 66, and inflatable collars 68 and 69, form the wound retractor. During use, an incision 50, e.g., in the shape of a slit (FIG. 2A) is first made in the patient's abdominal wall 52. Ring 64 and the attached portion of skirt 66 are then inserted into the body cavity through incision 50 with collars 68 and 69 being uninflated and remaining external to incision 50 (FIG. 2B). If ring 64 is circular and has a diameter less than the length of incision 50, it is inserted perpendicular to abdominal wall 52. Alternatively, if ring 64 is circular and its diameter is greater than the length of incision 50, ring 64 must be flexible enough to fit through incision 50 in a deformed state. Most preferably, ring 64 is rigid and has an elliptical shape with a maximum diameter longer than the length of incision 50 and a minimum diameter shorter than the length of incision 50. In this case, rigid ring 64 is inserted into the body cavity by orienting its minimum diameter parallel to incision 50.

Figure 2C:
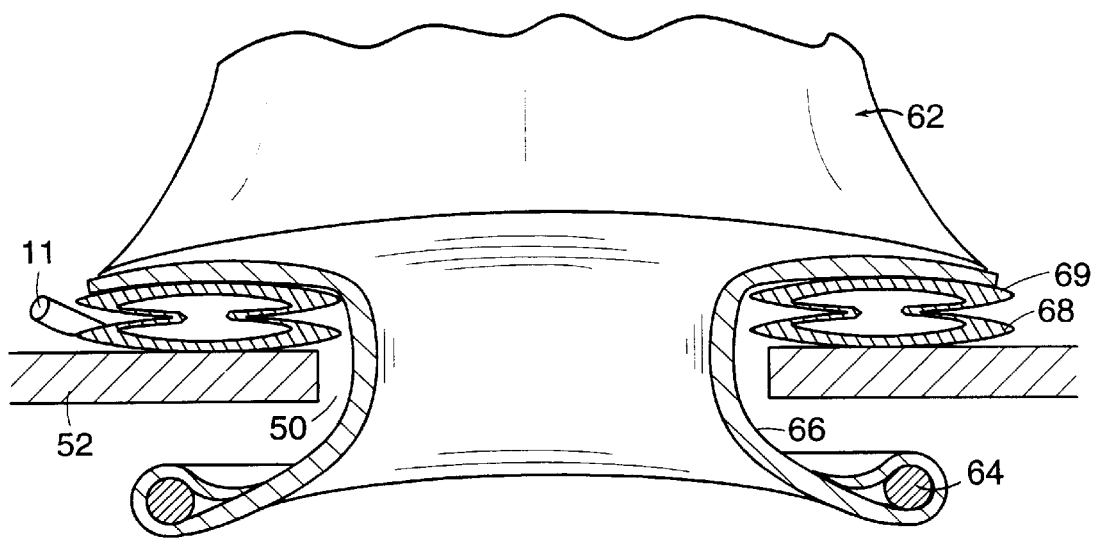
Figure 2D:
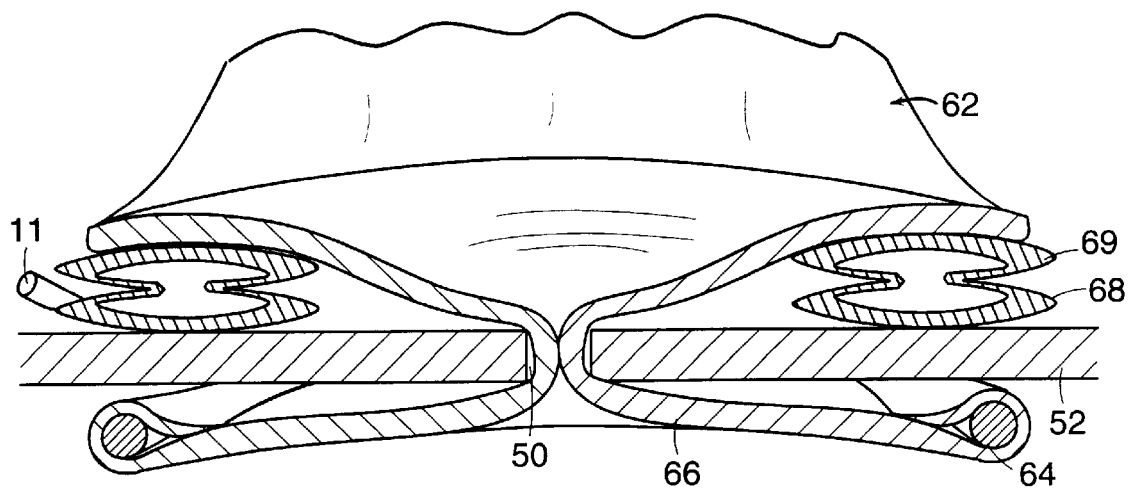
Figure 2E:
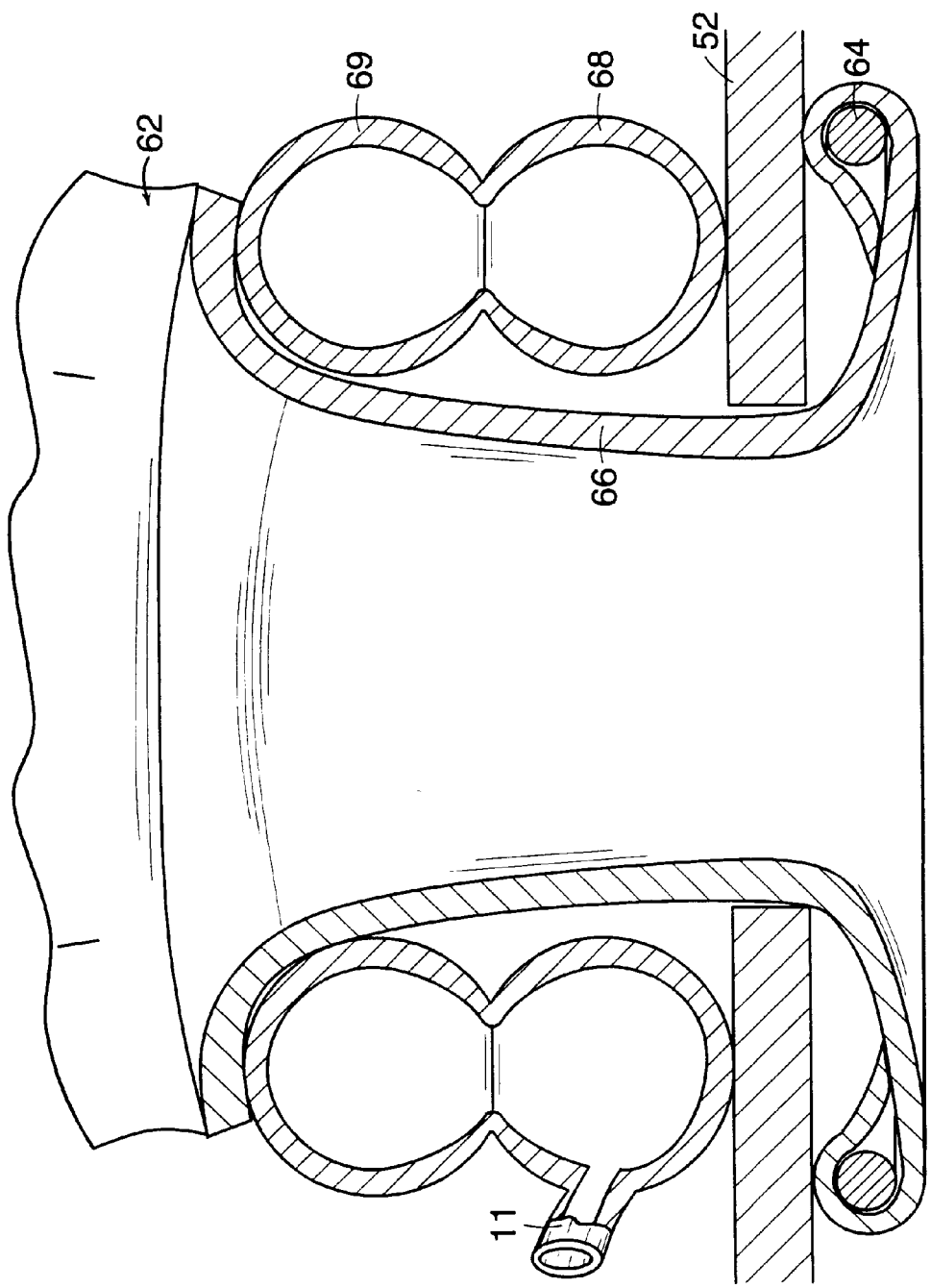

Once ring 64 is within the body cavity, it is oriented so that it is parallel to the abdominal wall 52 (FIGS. 2C and 2D). FIGS. 2C and 2D are cross-section views along the length and width, respectively, of incision 50, with collars 68 and 69 remaining uninflated. In this configuration, the diameter and stiffness of ring 64 are sufficient to prevent it from being pulled back through incision 50. The collars 68 and 69, which have diameters equal to or greater than the length of incision 50, are then inflated though inlet port 11. Collars 68 and 69 initially rest above abdominal wall 52 around incision 50. As collars 68 and 69 are inflated, they expand upward and their inner circumferences expand radially outwardly (FIGS. 2E). Since the upper end of skirt 66 is connected to the inner circumference of the upper-most collar 69, skirt 66 is also drawn upwards and radially outward, thereby drawing ring 64 tightly against the inner surface of abdominal wall 52. As a result, the intermediate portion of skirt 66 is drawn tightly against the edges of incision 50, retracting the adjacent tissue and producing an opening into the body cavity and a gas-tight seal between the body cavity and the remainder of access port 62. FIG. 2E illustrate a cross-sectional view of incision 50 with collars 68 and 69 being inflated.

Figure 3:
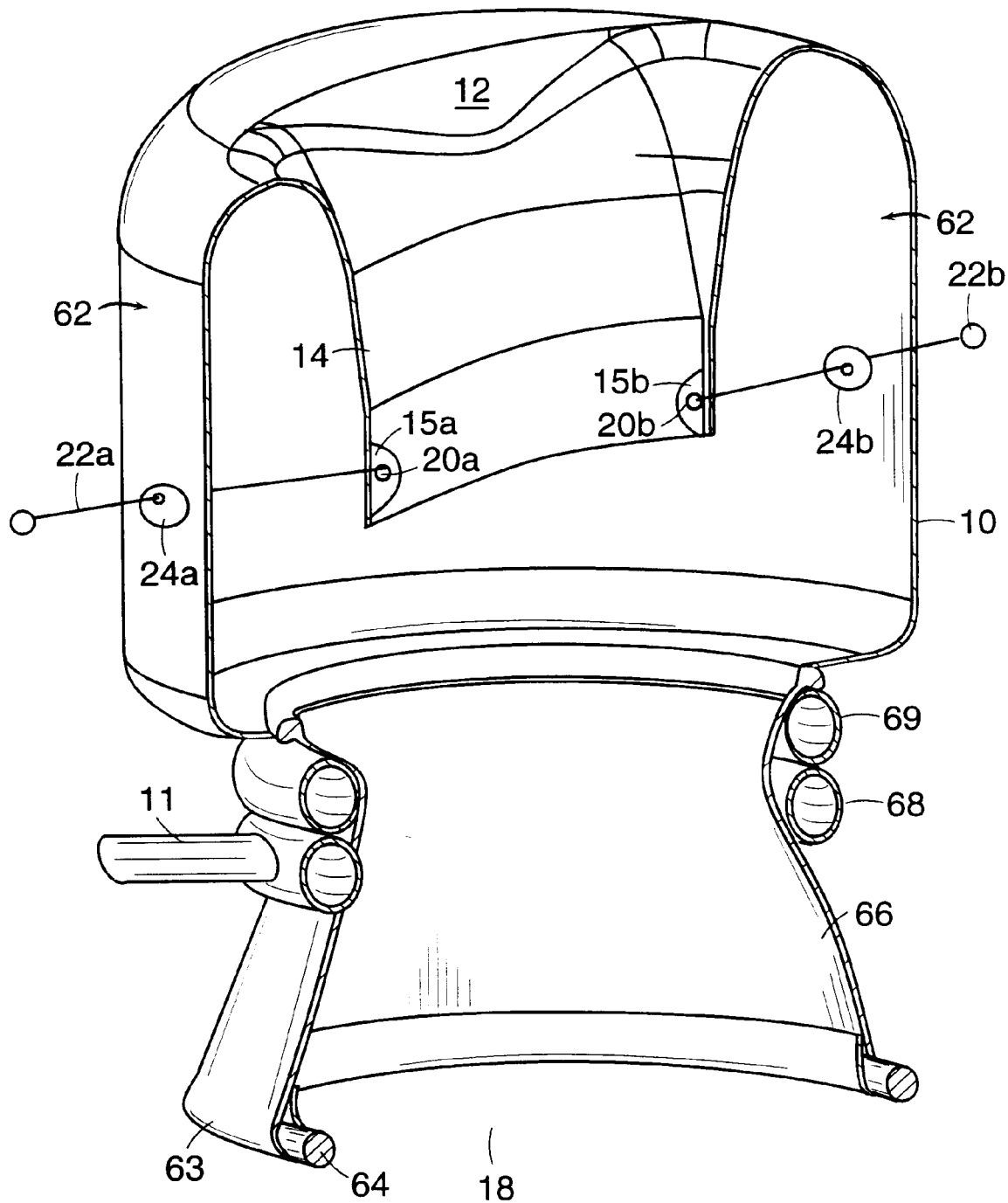
FIG. 3 is a cross-sectional view of another embodiment the surgical access port of FIG. 1.

Once the wound retractor of access port 62 has provided a gas-tight seal around incision 50, the body cavity is inflated with gas. The gas also expands into upper chamber 16, inflating the upper portion of access port 62. The pressure within upper chamber 16 seals flap valve 14, which prevents gas from escaping through entry opening 12. The portion of flap valve 14 distal to entry opening 12 has a preferred flattened orientation formed by heat sealing side portions 15a and 15b of flap valve 14 (FIG. 3). As the flap valve extends upward towards entry opening 12, it opens into an approximately circular geometry. During use, the surgeon inserts his hand into upper chamber 16 through entry opening 12 and flap valve 14. Insertion of the surgeon's hand momentarily breaks the seal between side portions 15a and 15b of flap valve 14, but thereafter the pressure within upper chamber seals flap valve 14 around the surgeon's arm. The loss of insufflation gases is thereby minimized during insertion and subsequent removal of the surgeon's hand. Since these gas losses are small, they can be compensated for easily by known pumping means used for inflating and regulating pressure in the body cavity.

To prevent flap valve 14 from everting as a result of positive pressure in the upper chamber, the portion of the access port extending from the upper portion of outer sleeve 10 toward flap valve 14 along entry opening 12 can be reinforced with additional material to stiffen the access port in this region, and to maintain the preferred orientation, i.e., to prevent eversion.

In addition or alternatively, heat-sealed side portions 15a and 15b can be provided with eyelet openings 20a and 20b through which drawstring 22a and 22b are attached (FIG. 3). Drawstrings 22a and 22b extend in opposite directions such that tension placed upon them pulls the two walls of flap valve 14 into close approximation. The drawstrings pass through the walls of outer sleeve 10 via drawstring ports 24a and 24b. Drawstring ports 24a and 24b form a friction fit around drawstrings 22a and 22b sealing upper chamber 16 from the surroundings and fixing the respective lengths of the drawstrings in upper chamber 16. Tension on drawstrings 22a and 22b can be increased by pulling on the drawstrings from the outside of outer sleeve 10, even as access port 62 is in use. In certain embodiments, drawstring ports 24a and 24b can further include one-way releasable locking mechanisms so that tension on the drawstrings can be increased and decreased from the outside of outer sleeve 10. The drawstrings prevent the inversion of flap valve 14 when upper chamber 16 is inflated and enhance the effectiveness of the flap valve seal, with and without insertion of a surgeon's hand.

In an alternative embodiment, drawstrings 22a and 22b are made of an elastic material and fixedly attached to the inner wall of outer sleeve 10. In this embodiment, the drawstrings do not extend outward through outer sleeve 10 and so the tension on them is not adjustable. Instead, the drawstrings are cut to a specific length to provide a preset tension on the flap valve opening when the upper chamber is fully expanded.

Figure 4:
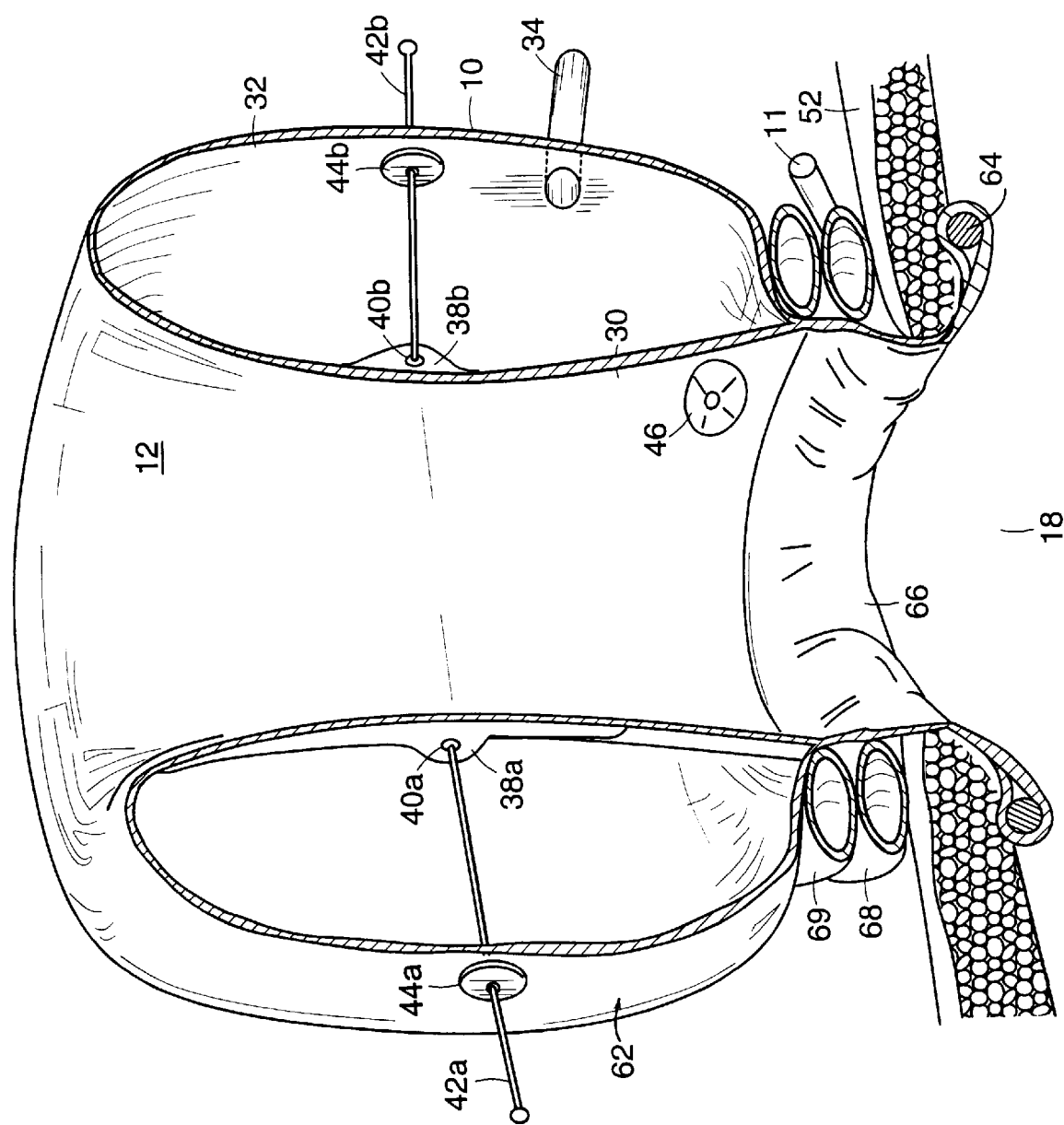
FIG. 4 is a cross-sectional view of another embodiment of a surgical access port.

FIG. 4 shows another embodiment of hand access port 62, which differs from the embodiments described previously in the following way. Flap valve 14 is replaced with a flexible and expandable inner sleeve 30 that extends from entry opening 12 and attaches to skirt 66 near the uppermost collar. As a result, upper chamber 32 is completely isolated from the body cavity and the surroundings. Instead of being inflated by insufflation gases from the body cavity, upper chamber 32 is inflated separately through inlet port 34.

The interior of inner sleeve 30 provides a channel from entry opening 12 to the wound retractor. When upper chamber 32 is inflated, the positive pressure in upper chamber 32 collapses together the walls of expandable inner sleeve 30, thereby sealing the channel, or alternatively, sealing inner sleeve 30 around the arm of a surgeon.

Inner sleeve 30 includes a central portion having a flattened orientation formed by heat sealing side portions 38a and 38b. Hence, the circumference of inner sleeve 30 begins substantially circular near entry opening 12, becomes elongate in the vicinity of side portions 38a and 38b, and becomes substantially circular again in the vicinity of collars 68 and 69. As described previously, the access port can also include eyelet openings 40a and 40b in side portions 38a and 38b, through which drawstrings 42a and 42b are attached, respectively. The drawstrings extend outwardly through drawstring ports 44a and 44b. When upper chamber 32 is inflated to a pressure greater than the pressure in the body cavity and the surroundings, the positive pressure collapses together the walls of inner sleeve 30 between side portions 38a and 38b, sealing the body cavity from entry opening 12. As a result of drawstrings 42a and 42b, this seal is enhanced.

During use of this embodiment, the wound retractor portion of access port 62 is implemented as described previously (and shown in FIGS. 2A–2E). Upper chamber 32 is then inflated, sealing the body cavity from the surroundings. Following this step, the body cavity is insufflated. If the pressure in the body cavity is greater than pressure in upper chamber 32, the seal will leak insufflation gas to the surroundings, otherwise the seal will be maintained. In this way, the isolated upper chamber 32 insures that the insufflation pressure in the body cavity will remain below the pressure in the upper chamber. As the surgeon inserts his hand through access port 62 and into the body cavity, the positive pressure from upper chamber 32 will force inner sleeve 30 to conform to the shape of the surgeon's arm, thereby maintaining the seal. As mentioned before, any loss of insufflation gas during the insertion and removal of the surgeon's hand can be compensated for by the insufflation pump.

Access port 62 may further include a one-way relief valve 46, such as a duck-billed relief valve, between upper chamber 32 and a region within inner sleeve 30 proximal to inflatable collars 68 and 69. A duck-billed relief valve is a one-way valve that opens when there is a sufficient pressure differential between opposite sides of the valve. In this embodiment, relief valve 46 would begin to leak if the pressure in upper chamber 32 became too large. For example, when the surgeon's arm is within inner sleeve 30, the volume of upper chamber 32 becomes compressed, thereby increasing the pressure within upper chamber 32 and against the surgeon's arm. This may be uncomfortable for the surgeon. Advantageously, relief valve 46 would optimize the effectiveness of the seal around the surgeon's arm and the comfort of the surgeon by releasing gas from upper chamber 32 to the body cavity. The insufflation pump used to inflate upper chamber 32 could compensate for any loss of gas from upper chamber 32 that may be required to maintain an effective seal once the surgeon removes his hand.

Relief valve 46 also allows the body cavity to be insufflated with the same pump used to inflate upper chamber 32. Once the pressure in upper chamber 32 reaches a preset value, gas will leak through relief valve 46 insufflating the body cavity. The seal between the entry opening and the body cavity will be maintained since the pressure in upper chamber will remain larger than the pressure in the body cavity. In a further embodiment, the access port includes a second one-way relief valve extending from inflatable collars 68 and 69 to the upper chamber. Thus, a single pumping means could be used to first inflate collars 68 and 69, then inflate upper chamber 32, and finally inflate the body cavity. The relief valves would require that the pressure in collars 68 and 69 is greater than the pressure in upper chamber 32, which is greater than the pressure in the body cavity.

A relief valve may also be positioned between upper chamber 32 and a region of inner sleeve 30 proximal to entry opening 12. In this case gas will leak for the upper chamber into the surroundings.

Access Port Variations

In another embodiment, the access port described above having an inner and outer sleeve can also include a second pair of drawstrings for imparting a second region of the inner sleeve with a preferred flattened geometry. Thus, when the seal formed by the first flattened region is broken during the insertion or removal of a surgeon's hand, pressure from the inflated upper chamber provides a second seal at the second flattened region, or vice-versa.

Alternatively, for any of the embodiments described previously, a flap valve can be connected to the skirt and extend into the wound retractor, thereby providing a second seal on the surgeon's arm. Thus, when the surgeon's hand breaks either seal, the remaining seal prevents the escape of insufflation gases.

Figure 5:
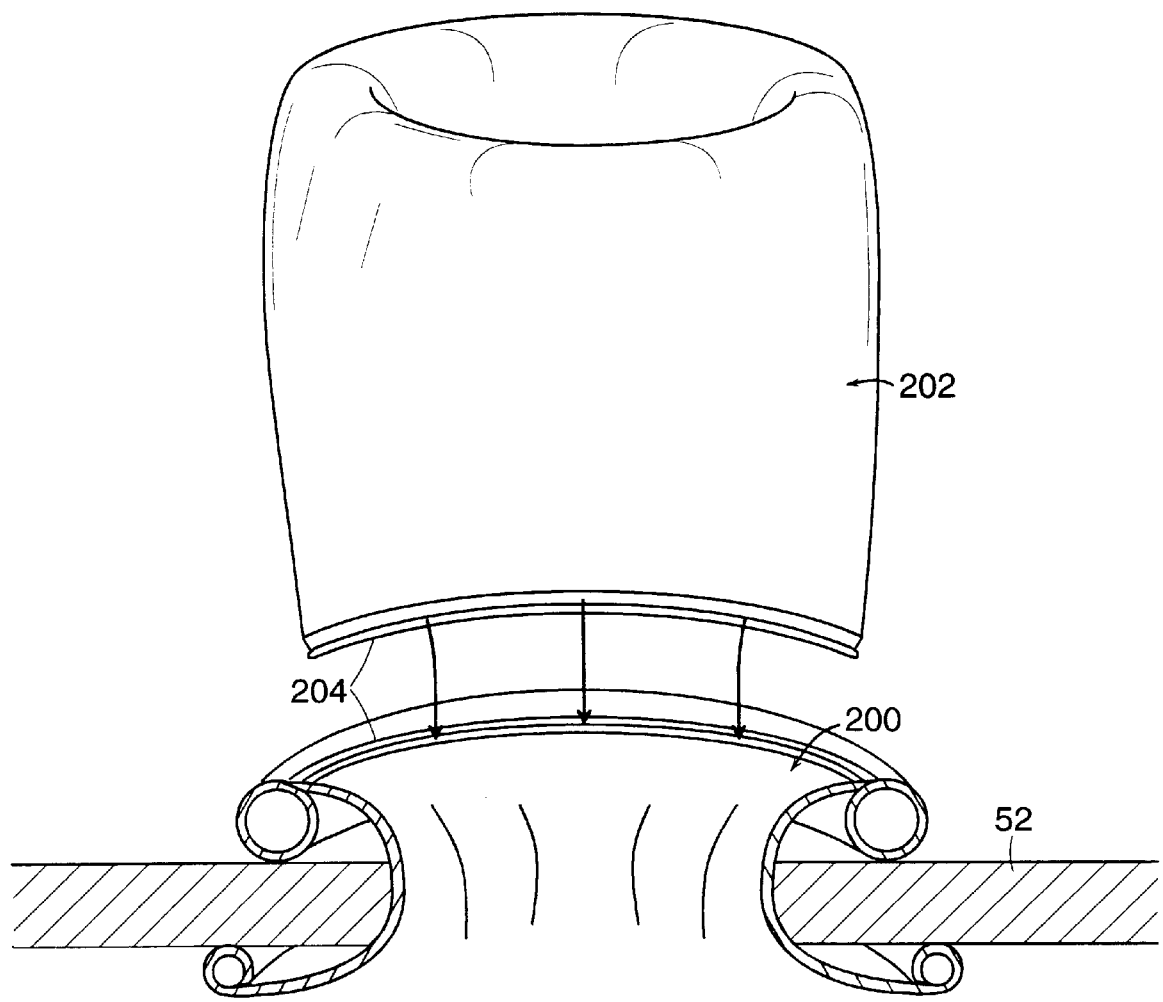
FIG. 5 is a schematic of a modular surgical access port.

In a further embodiment, the surgical access port can be modular as shown in FIG. 5, comprising a wound retractor 200 (as described above) and a sealing sleeve 202. Depending on the particular embodiment, the sealing sleeve could, for example, include an outer sleeve having a flap valve seal within an entry opening (e.g., the embodiment shown in FIG. 1) or an inflatable chamber formed between an inner and outer sleeve (e.g., the embodiment shown in FIG. 4). For surgical procedures that do not require insufflation of the body cavity, the wound retractor can be used on its own for retracting an incision to make an opening into the body cavity. When insufflation of the body cavity is necessary, the sealing sleeve is attached to the wound retractor using a reusable gas-tight attachment means 204, such as a zip-lock seal. Alternatively, for example, the attachment means can include a compression or threaded fit between a pair of semi-rigid collars attached to the sealing sleeve and wound retractor, respectively. Otherwise, the surgical access port is structured and functions similarly to the embodiments described above.

Figure 6A:
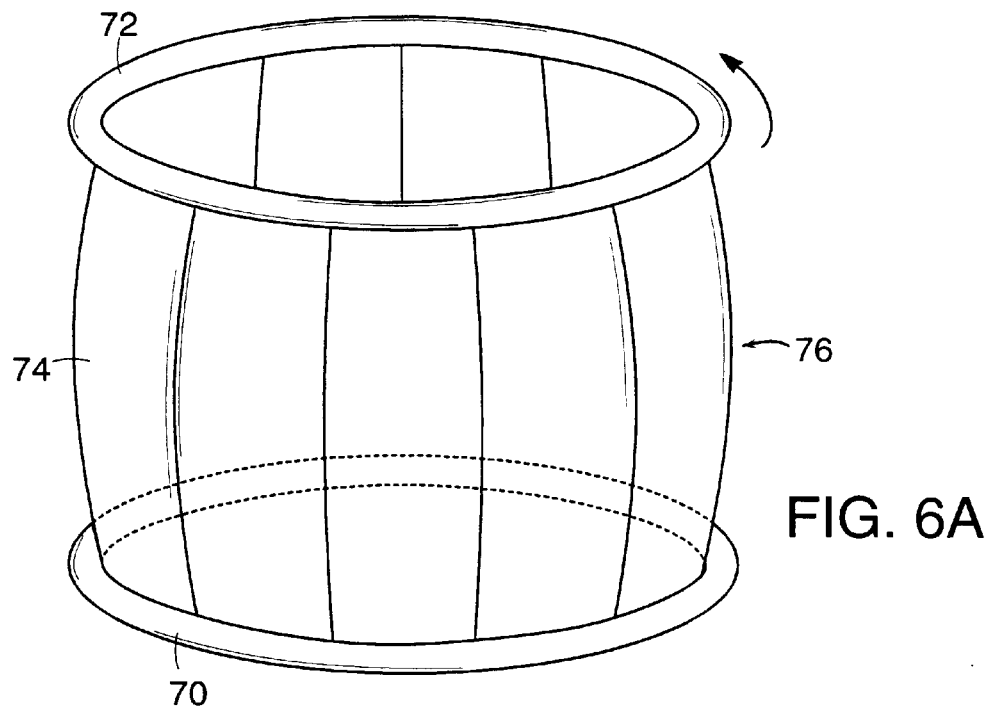
FIGS. 6A and 6B are schematic views of an iris valve in open and closed configurations, respectively.
Figure 6B:
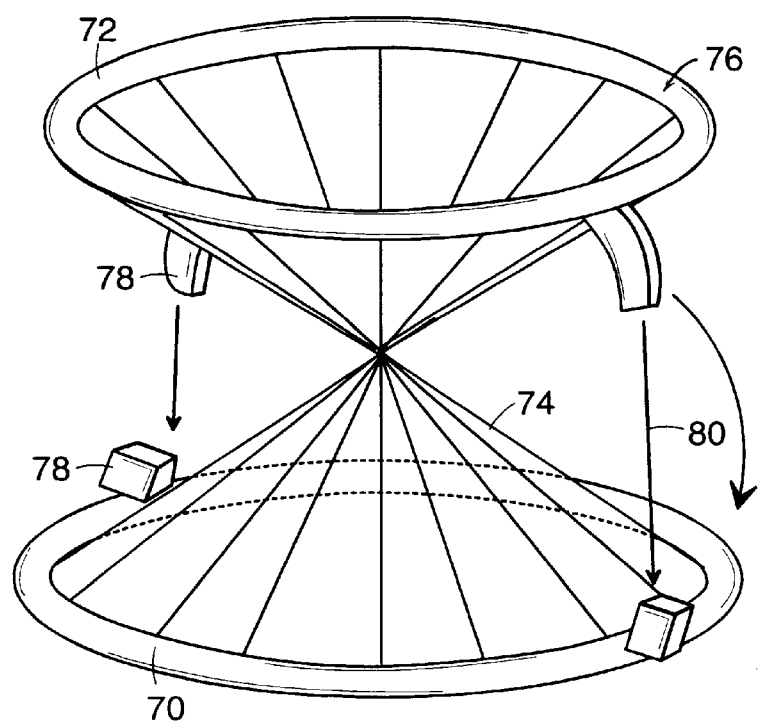

In other embodiments, the wound retractors described herein can be used with other types of sealing sleeves. In particular, rather than sealing means based on inflation, mechanical sealing means well known in the art can be provided. For example, as shown in FIGS. 6A and 6B, the sealing sleeve can include an iris valve 76 attached to the upper end of the skirt above the inflatable collars. The iris valve is formed from two stiff rings 70 and 72 attached to opposite ends of a tubular piece 74 of elastic material (FIG. 6A). In this configuration, iris valve 76 is open. To seal the opening, or alternatively, to seal around a surgeon's arm inserted through the opening, the upper ring 72 is rotated relative to the lower ring 70, as a result tubular piece of elastic material 74 becomes twisted and the opening through the tubular piece contracts (FIG. 6B). To lock the relative positions of the upper and lower rings, the rings are attached to one another using a clasping mechanism 78 and 80, e.g., a latch.

Alternatively, for example, the lower ring can be provided with upright pegs evenly spaced around its circumference. The upright pegs fit into corresponding openings in the upper ring, so that when the upper ring is placed on the lower ring the rotational position of the rings relative to one another is fixed.

Another embodiment of a sealing sleeve 101 is shown in FIGS. 7A and 7B. The top end 108 of sleeve 10 is maintained in an open configuration by its connection to a rigid ring 110. Just below rigid ring 110, the inner wall of sleeve 100 is connected to an inflatable cuff 112, which is made out of an expanding, elastomeric material (e.g., rubber). Surrounding inflatable cuff 112 on the outside of sleeve 10 is a stiff backing 100 of a close-fitting non-expanding material (e.g., a nylon weave). Since backing 100 is non-expanding, cuff 112 will expand inward when inflated, thereby sealing around a surgeon's arm when the surgeon's hand is inserted through the channel formed by wound retractor 106. Furthermore, since there is a region of flexible material between cuff 112 and wound retractor 106, the surgeon can easily alter the angle of his arm and the penetration depth of his hand, without jeopardizing the seal formed by cuff 112. When the surgeon's hand is removed from the access port, cuff 112 can be inflated further to completely seal the channel.

Alternatively, to seal the channel when the surgeon's hand is removed, rigid ring 110 can receive a snap-on cap 114 (FIG. 7B), which covers the opening at the top end 108 of sleeve 100. The cap is made of a semi-flexible material, which includes, for example, hard rubber, polyvinyl chloride (PVC), and foam. Cap 114 includes a groove 117, above a lower inner lip 116, that mates with rigid ring 110. The mechanical pressure created by a slight undersizing of the diameter of groove 117 above inner lip 116 relative to the diameter of rigid ring 110 forms a tight seal. Cap 114 can also include instrument ports 118 and 120, which provide gas-tight sealable openings into the body cavity for surgical instruments (e.g., trocars, cannulas, and endoscopes).

Figure 8:
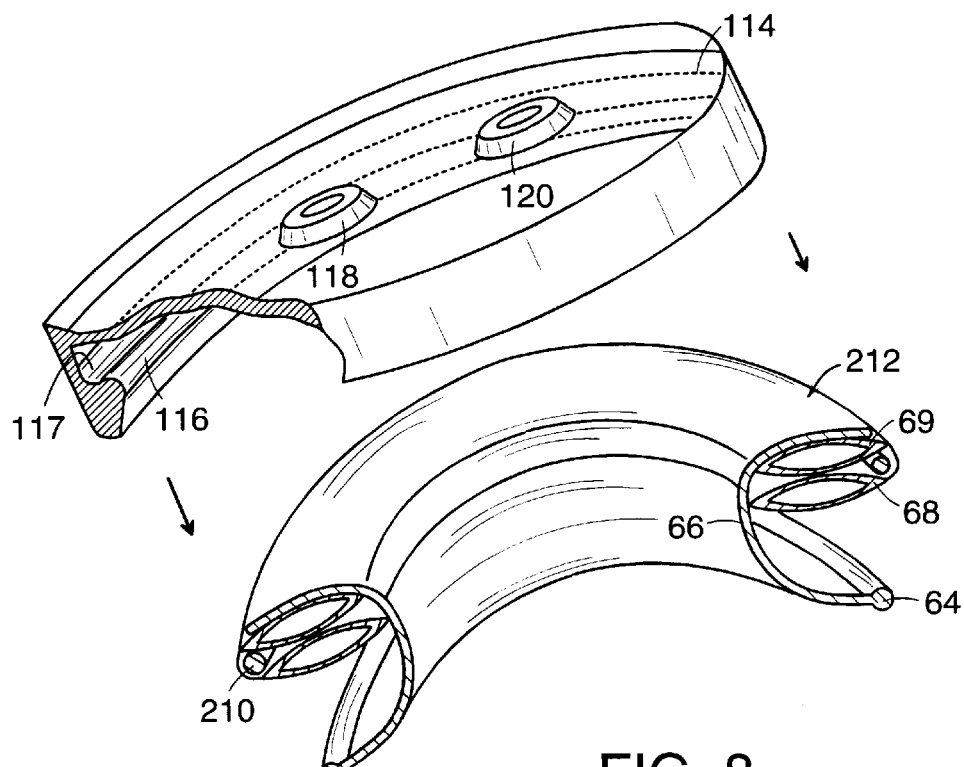
FIG. 8 is a cross-sectional view of an embodiment of a wound retractor.

In another embodiment, shown in FIG. 8, the wound retractor described previously can further include a rigid ring 210 surrounding the outer perimeter of inflatable collars 68 and 69. For example, skirt 66 can extend over, and connect to, the outer perimeter of inflatable collars 68 and 69, enclosing rigid ring 210 between these collars. Alternatively, for example, one of the inflatable collars can include additional material for enclosing rigid ring 210 around the outer perimeter of that collar. Rigid ring 210 will help prevent collars 68 and 69 from deforming in response to forces from the retracted opening when inflated, and will provide structure to the top part of a wound retractor 212 when collars 68 and 69 are uninflated. Furthermore, rigid ring 210 allows snap-on cap 114 to directly cover the channel provided by wound retractor 212. Cap 114 is mounted onto ring 210 by a compression fit. The diameter of rigid ring 210 is slightly larger than the diameter of groove 117 above lower lip 116, thereby forming a tight seal.

Figure 9:
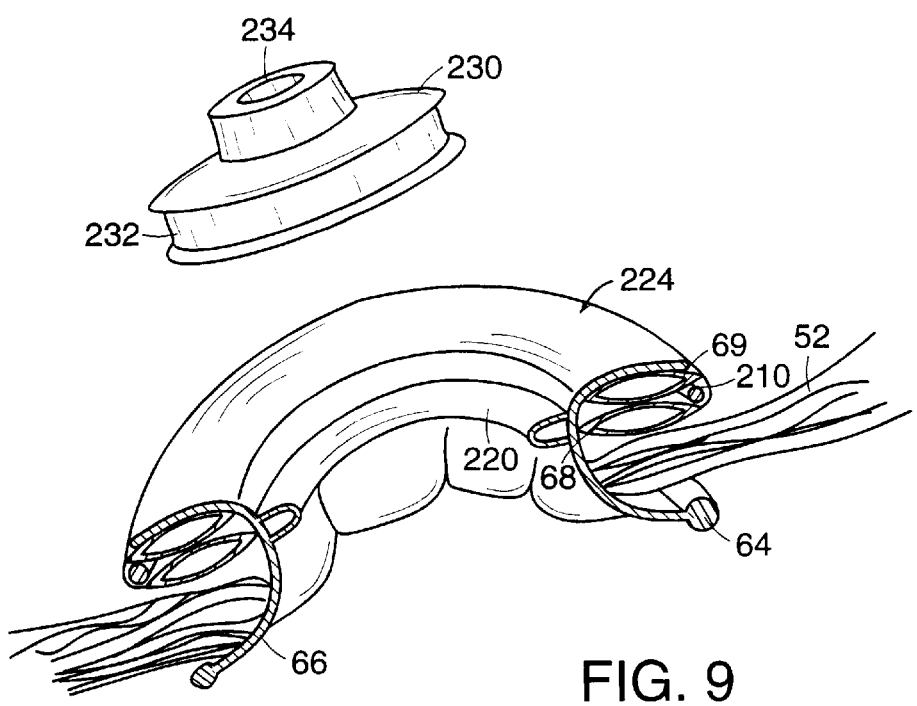
FIG. 9 is a cross-sectional view of another embodiment of a wound retractor.

As shown in FIG. 9, wound retractor 224 can further include an inflatable cuff 220 attached directly to skirt 66 of the wound retractor adjacent to the inner perimeter of inflatable collars 68 and 69. In this case, wound retractor 224 includes a sealing means for the channel into the body cavity (i.e., cuff 220) and a sealing sleeve is unnecessary. Cuff 220 is made of an expandable, elastomeric material and will expand inward when inflated, sealing around a surgeons arm that is inserted through the channel formed by wound retractor 224. When the surgeon's arm is removed, cuff 220 can either be inflated to completely seal the channel, or alternatively, cuff 220 can receive a sealing plug 230. After plug 230 is inserted into wound retractor 224, inflated cuff 220, when inflated, fits securely within recessed groove 232, thereby sealing the channel. As with cap 114, sealing plug 230 can include one or more sealable instrument ports 234 for inserting instruments into the body cavity through wound retractor 224.

Access Port Variations using a Glove

Figure 10:
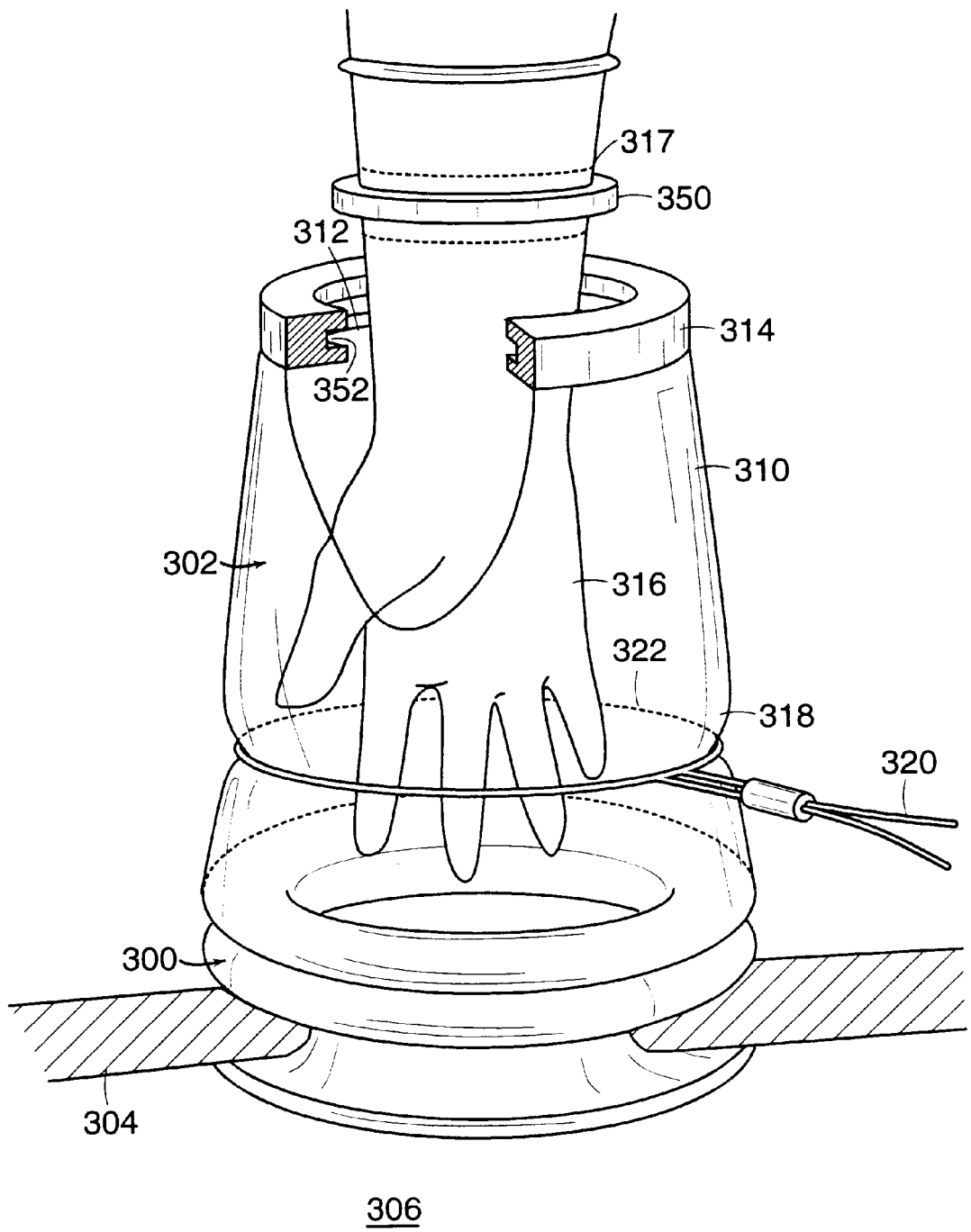
FIG. 10 is a perspective view of an embodiment of the access port employing a glove.
Figure 11:
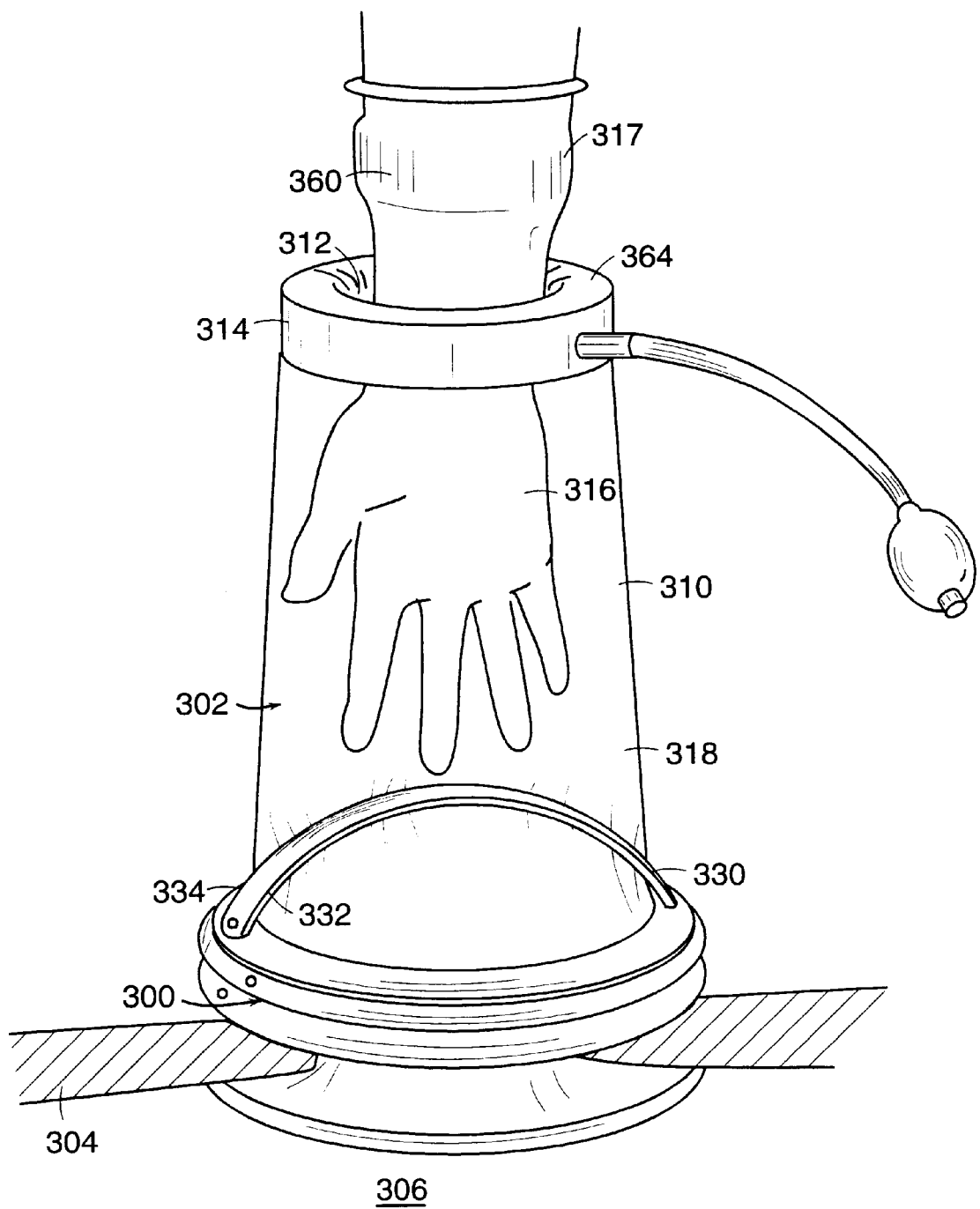
FIG. 11 is a perspective view of another embodiment of the access port employing a glove.
Figure 12:
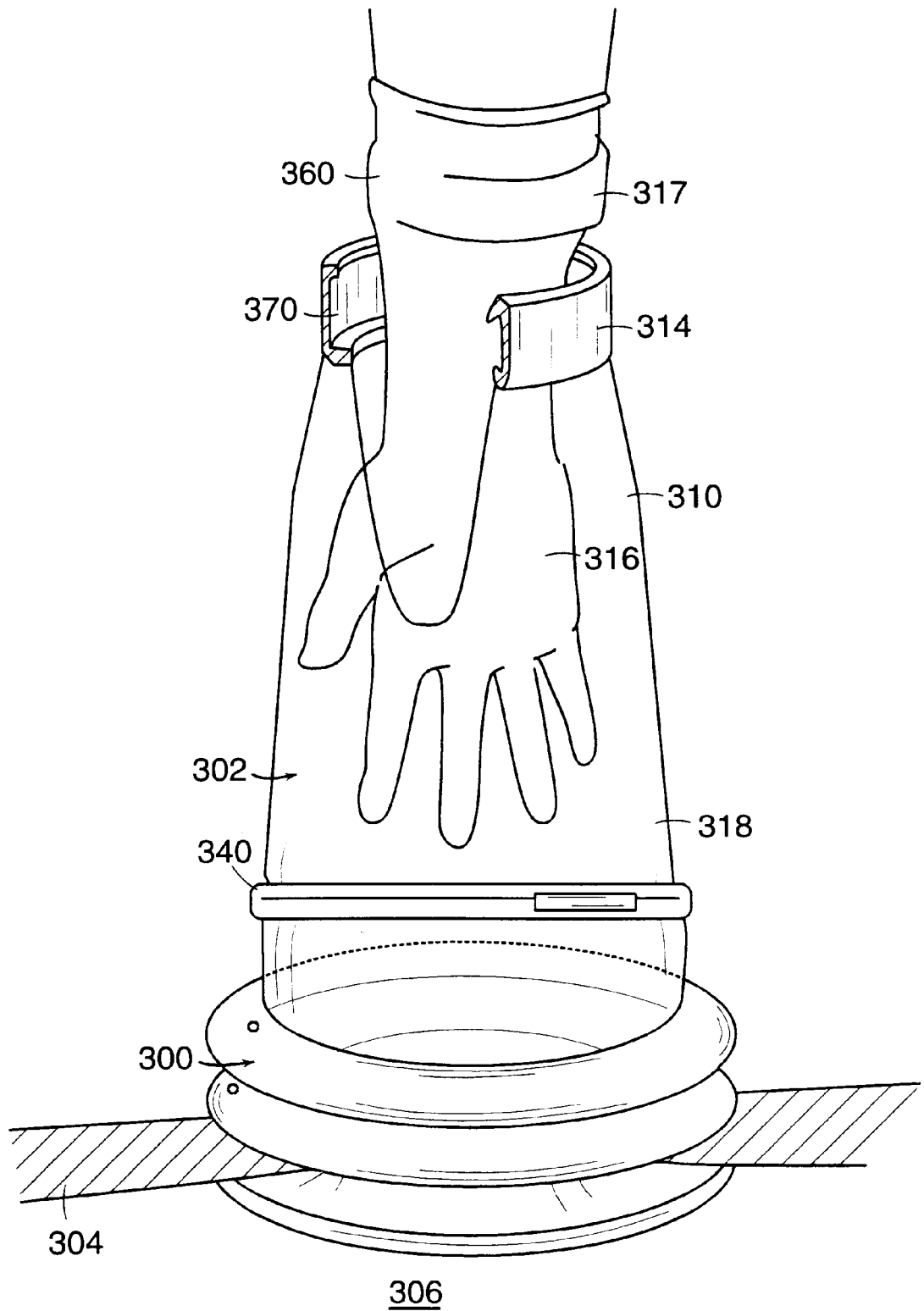
FIG. 12 is a perspective view of a further embodiment of the access port employing a glove.

In another series of embodiments shown in FIGS. 10–12, a seal is made between the cuff of a glove worn by the surgeon and the opening of the sealing sleeve. A wound retractor 300 of an access port 302 provides an opening through an abdominal wall 304 into a body cavity 306. A flexible tubular sleeve 310 is attached to wound retractor 300 external to body cavity 306, extending the channel formed by wound retractor 300 to an entry opening 312 of sleeve 310. A sealing collar 314 is connected to sleeve 310 surrounding entry opening 312. Sealing collar 314 is for mating to an enlarged cuff 317 of a glove 316 worn by a surgeon, thereby sealing the channel from the surroundings.

Sleeve 310 can be provided with a means for closing the channel along an intermediate portion 318 of sleeve 310 to seal the opening to body cavity 306. For example, along a circumference 322 of intermediate portion 318, sleeve 310 can attach to a drawstring 320, which can be drawn up external to sleeve 310 (FIG. 10). When drawstring 320 is drawn up, circumference 322 contracts until the channel into body cavity 306 is completely covered by sleeve 310. In another embodiment, shown in FIG. 11, intermediate portion 318 can be closed by a "bear-trap" clamp 330 comprising two hinged arcuate bands 332 and 334 connected to the base of sleeve 310. When bands 332 and 334 extend away from one another, they surround the base of sleeve 310 and the channel remains open. As bands 332 and 334 are brought together above wound retractor 300, they force together opposite inner surfaces of sleeve 310, thereby closing the channel and sealing the opening to body cavity 306.

In a further embodiment, shown in FIG. 12, inner surfaces of intermediate portion 318 of sleeve 310 include a zip-lock seal 340 for sealing the opening to body cavity 306. In other embodiments, a separate mechanical clamp can be used to hold inner surfaces of intermediate portion 318 together, thereby closing the channel.

During use, the closing means is used to seal the opening into body cavity 306 formed by wound retractor 300. Body cavity 306 is then insufflated, with the closing means preventing the escape of insufflation gases into the surroundings. Cuff 317 of surgeon's glove 316 is then mated with sealing collar 314 and the closing means is released so that the surgeon's gloved hand can access body cavity 306. The open end of sleeve 310 is sealed to enlarged cuff 317, preventing the escape of insufflation gases even though the closing means surrounding intermediate portion 318 is not in use. The length of flexible sleeve 310 provides the surgeon's arm with a sufficient movement range. When the surgeon brings his gloved hand above intermediate portion 318, the closing means can be reset, thereby resealing the opening to body cavity 306. Thereafter, enlarged cuff 317 is detached from sealing collar 314 and the surgeon's gloved hand is removed from access port 302.

In one embodiment, enlarged cuff 317 includes a radially-outwardly extending flange 350 that mates with an inner groove 352 within sealing collar 314. Flange 350 is made of a semi-rigid material (e.g., plastic or rubber) that is sufficiently deformable for flange 350 to be inserted into sealing collar 314 and mate with groove 352 (FIG. 10).

In the above embodiment, glove 316 can be a standard surgical glove and flange 350 can be formed by placing a bracelet over the surgeon's gloved hand and mounting the bracelet to the wrist portion of the glove using an adhesive material. In order to seal the channel, the bracelet is designed to mate with groove 352.

Alternatively, a bracelet 360 can be worn underneath glove 316 (FIGS. 11–12). Again, glove 316 is a standard surgical glove, which is typically made of a flexible and semi-elastic material (e.g., latex, natural rubber, or polymeric materials). In this case, the surgeon places a bracelet 360 around his wrist and then pulls glove 316 over his hand and the bracelet. Glove 316 conforms to the shape of bracelet 360, thereby forming enlarged cuff 317, which completely surrounds the wrist of the surgeon and can mate with sealing collar 314.

In these embodiments, bracelet 360 is made of a substantially rigid or semi-rigid material (e.g., an o-ring made of hard rubber) and has a fixed diameter. Sealing collar 314 can comprise an inflatable bladder 364 for expanding against and mating with enlarged cuff 317 (FIG. 11). Sealing collar 314 can also be made of a semi-compressible material (e.g., foam or a gel-filled bladder), which provides an interference fit with enlarged cuff 317. Alternatively, bracelet 360 can have a cross-sectional shape designed to fit with an inner groove 370 of sealing collar 314 (FIG. 12). Glove material pressed between fitted collar 314 and bracelet 360 functions as a gasket, enhancing the effectiveness of the seal.

In any of the embodiments using the bracelet and glove, the seal is maintained without constricting the surgeons arm, which can be a source of discomfort. The surgeon's arm is not constricted because bracelet 360 has a fixed diameter and need only fit loosely around the surgeon's arm. However, by mating with sealing collar 314, bracelet 360 securely attaches glove 316 to entry opening 312 of sleeve 300, sealing the opening to the body cavity, and allowing access to the body cavity via glove 316.

Preventing the constriction of a surgeon's arm can be further achieved by an embodiment in which the cross-sectional diameter of bracelet 360 along the length of the surgeons arm is slightly larger than the corresponding dimension of groove 370. Hence, an interference fit between the mating components is provided along a direction parallel to the surgeon's arm, and bracelet 360 is not compressed along a direction that will constrict a surgeon's arm.

In some embodiments, it is desirable for the diameter of bracelet 360, and the glove itself, to be large enough that the surgeon can remove his hand from glove 316 without detaching glove 316 from sleeve 310. In this case, access port 300, glove 316 and bracelet 360 combine to form a detachable glove box, in which, during use, the surgeon can insert and remove his hand from the body cavity at will (via glove 316) with no loss of insufflation gas, and when the procedure is completed, glove 316 can be detached from access port 300.

It is worth pointing out, however, that the diameter of bracelet 360 should not be too large to prevent a surgeon's range of movement. In particular, the diameter of enlarged cuff 317 formed by bracelet 360 should be smaller than the diameter of the retracted incision. As a result, the surgeon can completely insert his gloved hand and arm, including enlarged cuff 317, through the retracted opening into the body cavity. Alternatively, the glove and cuff can be designed such that the glove extends up to, for example, a surgeon's elbow, and the cuff fits around the surgeon's upper forearm or elbow to provide the surgeon a sufficient reach inside the body cavity.

In other embodiments, a separate mechanical or elastic clamp can be used to attach glove 316 to the entry opening 312 of sleeve 310. Furthermore, in any of the above embodiments, additional mechanical or elastic, clamping or tightening means (e.g., elastic bands, drawstrings, or incremental tightening rings) can be used to enhance the seal provided by the connection of enlarged cuff 317 to sealing collar 314.

Inclusion of a Light Source

Figure 13:
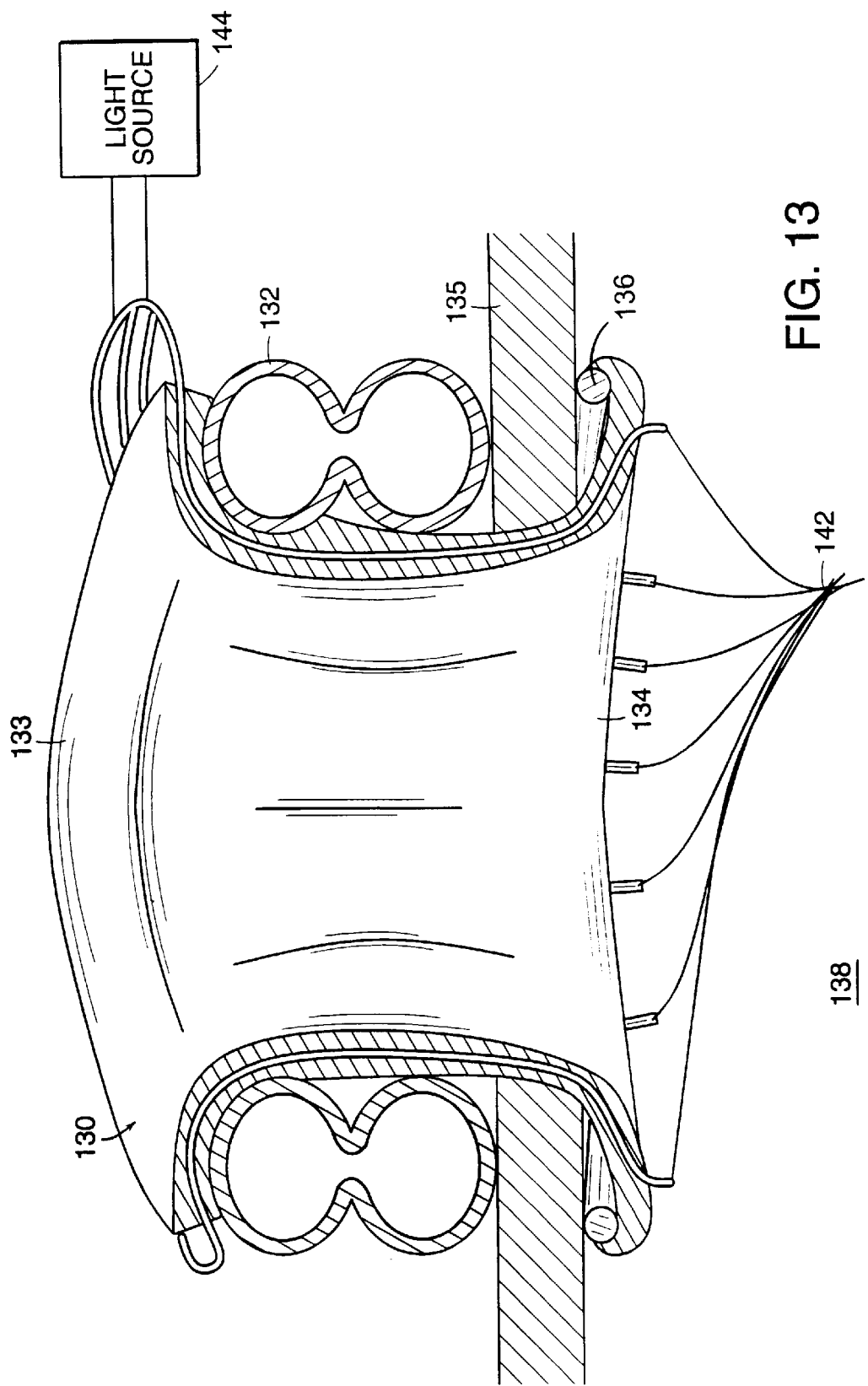
FIG. 13 is a schematic of a wound retractor having a light source for illuminating the body cavity.

In further embodiments, any of the embodiments described previously can include a light source connected to a portion of the wound retractor inserted into and facing the body cavity. For example, referring to FIG. 13, a wound retractor 130 includes inflatable collar 132 surrounding an entry opening 133 external to a patient's abdominal wall 135, a skirt 134 extending from uppermost collar 132 through an incision into a body cavity 138, and a ring 136 reinforcing the substantially circular opening of the end of skirt 134 distal to uppermost collar 132. Encased within skirt 134 is a plurality of optical fibers 142 extending along the length of skirt 134 toward ring 136. The optical fibers can also be adhered to the inner or outer walls of skirt 134. The ends of fiber optic cables 142 face into the body cavity and extend around the perimeter of exit opening 140 adjacent to ring 136. The optical fibers 142 pass through skirt 134 to the outer perimeter of entry opening 133 where they are bundled together and connected to an external light source 144.

Other light sources can also be used. For example the ring could be luminescent and the skirt pocket transparent. In particular, the ring could be electroluminescent, so that when a current or a voltage is applied, the ring emits light. Wire used to pass current or voltage into the ring could be encased in the skirt as was described above for fiber optic cables. In another embodiment, the ring material is phosphorescent and is "charged-up" by it exposing it to light, e.g., ultraviolet light, prior to use. In a further embodiment, the ring could enclose chemiluminescent material. In this case, a seal within the ring is ruptured immediately prior to use, thereby mixing a plurality of materials that react with one another and emit light from the ring.

Materials and Manufacture

In the above embodiments, a gas-tight, flexible, and partially elastic material, such as a plastic or a rubber, is used for the skirt, collars, and the inner and outer sleeves. For example, polyethylene, polypropylene, urethane, natural rubber, or latex can be used. The material for the ring provides stiffness to the lower end of the skirt. In particular, the ring should be stiff enough that it will not pass through the incision when it is initially parallel to the inner wall of a patient's skin and a force is drawing it tight against the inner wall. The ring can be made of, e.g., metals, polyvinyl chloride (PVC), hard rubber, and foam. Alternatively, the hem-shaped pocket could be gas-tight and the ring pneumatic, with the pocket being filled with a gas, liquid, or gel. During use, the pocket is filled prior to the insertion of the exit opening into the body cavity. Methods of molding or heating-sealing together flexible plastic materials into prescribed medically-approved objects are well known in the art and can be carried out by commercial entities (e.g., Dielectrics Industries, Chicopee, Mass.).

OTHER EMBODIMENTS

It is to be understood that while the invention has been described in conjunction with the detailed description thereof, that the foregoing description is intended to illustrate and not limit the scope of the invention, which is defined by the scope of the appended claims. For example, the surgical access port can also be used and adapted for insertion of a surgical tool rather than, or in addition to, a surgeon's hand. Moreover, the sealing sleeve can be provided with a plurality of access openings to simultaneously accommodate a plurality of hands and/or instruments that are be inserted into the body cavity. Also, the rings, collars and entry and exit openings, are not limited to substantially circular shapes, instead they could, for example, have an elliptical shape to better accommodate the inserted object and provide the desired retraction of the incision. Furthermore, the length of the sealed side portions in the sealing sleeve can also be optimized to more effectively seal the inserted object.

The retractor and sealing sleeve are not limited to surgical applications. They can be used in any application in which the edges of an incision into a surface is retracted into an opening, and where appropriate, a seal is used to prevent the escape of gases through the opening.

Other aspects, advantages, and modifications are within the scope of the following claims.

What is claimed is:

1. A device for retracting edges of an incision in a surface to form an opening, the device comprising:
    a flexible, tubular skirt having an upper end, a lower end, and a channel therebetween;
    a non-inflatable ring connected to the lower end of the skirt for maintaining the lower end in an open configuration and defining an exit opening to the channel, wherein the ring is designed to fit through the incision and remain under the surface when it is oriented parallel to surface and is configured to contact an underside of the surface; and
    an inflatable collar connected to the skirt and surrounding the upper end, wherein the collar, when fully inflated, maintains the upper end in an open configuration and defines an entry opening to the channel.

2. The device of claim 1, wherein the collar when fully inflated has an inner aperture having a diameter greater than the length of the incision.

3. The device of claim 1, further comprising a light source connected to the lower end of the skirt.

4. The device of claim 3, wherein the light source is a fiber optic cable.

5. The device of claim 1, wherein the skirt includes a hem-shaped pocket that encloses the ring.

6. The device of claim 1, wherein the ring has a substantially elliptical shape.

7. The device of claim 1, further comprising a second ring adjacent to an outer perimeter of the inflatable collar for reinforcing the entry opening.

8. The device of claim 7, further comprising a detachable cap for sealing the entry opening, wherein the detachable cap is adapted to be received by the second ring.

9. The device of claim 1, further comprising an inflatable cuff connected to an inner wall of the skirt and surrounding the entry opening for sealing around a surgeon's arm inserted into the channel.

10. The device of claim 9, further comprising a detachable plug covering the entry opening, wherein the detachable plug is adapted to be received by the inflatable cuff.

11. A surgical access port comprising:
    the device of claim 1; and
    a flexible sleeve connected to at least one of the inflatable collar and the skirt, extending the channel from the exit opening of the skirt to an open end of the flexible sleeve distal to the skirt.

12. The access port of claim 11, wherein the flexible sleeve can be removed and reattached to the device of claim 1.

13. The access port of claim 11, wherein the flexible sleeve includes an inner sleeve and an outer sleeve forming a chamber therebetween, and an inlet port for inflating the chamber, whereby inflating the chamber compresses together a central portion of the inner sleeve, thereby sealing the channel.

14. The access port of claim 13, further comprising a pair of drawstrings attached to opposite sides of the central portion of the inner sleeve and pulling the sides in opposite directions toward the outer sleeve, thereby collapsing the central portion of the inner sleeve into two flattened portions contacting each other to form a seal.

15. The access port of claim 13, wherein the central portion of the inner sleeve includes two sealed regions opposite one another in which immediately adjacent portions of the inner sleeve are welded together, thereby dividing the central portion into two substantially flattened portions extending along the length of the channel adjacent to one another.

16. The access port of claim 11, further comprising a flap valve that connects to the open end of the flexible sleeve and extends into the channel, wherein the flap valve seals the channel when there is a positive pressure differential between the channel and the surroundings.

17. The access port of claim 16, further comprising a pair of drawstrings attached to opposite ends of the flap valve and pulling the ends in opposite directions to enhance the sealing ability of the flap valve.

18. The access port of claim 11, further comprising a light source connected to the skirt in the vicinity of the exit opening.

19. The access port of claim 11, wherein the flexible sleeve comprises an iris valve.

20. The access port of claim 11, further comprising an inflatable cuff attached to an inner surface of the sleeve for sealing around a surgeon's arm.

21. The access port of claim 20, wherein the inflatable cuff is surrounded by a backing of a substantially non-expandable material.

22. The access port of claim 21, further comprising a second ring connected to the sleeve and surrounding the open end of the sleeve.

23. The access port of claim 22, further comprising a detachable cap for sealing the open end of the sleeve, wherein the detachable cap is adapted to be received by the second ring.

24. The access port of claim 11, further comprising:
a sealing collar attached to the sleeve and surrounding the open end, said sealing collar having a groove along its inner perimeter; and
a glove comprising a flange at the open end of the glove that mates with the groove and seals the channel when inserted into the groove.

25. The access port of claim 11, further comprising:
a sealing collar attached to the sleeve and surrounding the open end, said sealing collar including an inwardly expanding inflatable bladder; and
a glove having an enlarged cuff, wherein when the glove is inserted into the sleeve, the enlarged cuff mates with the inflated bladder and seals the opening.

26. The access port of claim 11, further comprising:
a sealing collar attached to the sleeve and surrounding the open end, said sealing collar having a groove along its inner perimeter;
a bracelet having a fixed diameter that mates with the groove; and
a glove, wherein during use the bracelet is worn by a surgeon underneath the glove and is mated to the sealing collar, a portion of the glove being held within the groove by the bracelet, thereby sealing the channel.

27. A surgical access port, for use with a surgical glove, comprising:
a device for retracting the edges of a surgical incision to form an opening into a patient's body cavity;
a sealing sleeve attached to the device external to the body cavity, wherein the sealing sleeve comprises,
a flexible sleeve providing a channel from its open end distal to the retracting device through to the opening, and
a sealing collar attached to the sleeve and surrounding the open end; and
a semi-rigid bracelet separable from the glove and having a fixed diameter that releasably mates with the sealing collar, the bracelet being configured to fasten a portion of the glove to the sealing collar when worn beneath the glove and mated to the sealing collar.

28. The access port of claim 27, further comprising the glove.

29. A method of using the surgical access port of claim 27, comprising the steps of:
placing the bracelet around an arm of the surgeon;
placing the glove over a hand of the surgeon so that the glove extends over the bracelet;
inserting the gloved hand into the access port; and
attaching the portion of the inserted glove to the access port by mating the bracelet with the sealing collar of the access port.

30. A surgical access port comprising:
a device for retracting the edges of a surgical incision to form an opening into a patient's body cavity, the retracting device comprising an upper portion for overlying tissue surrounding the incision, a lower portion for underlying the tissue surrounding the incision, and a flexible skirt connecting the upper and lower portion, all of which permit the retracting device to form a gas-tight seal with the edges of the incision; and
a sealing sleeve attached to the device external to the body cavity, wherein the sealing sleeve comprises:
a flexible sleeve providing a channel from its open end distal to the retracting device through to the opening; and
drawstrings connected to the flexible sleeve for sealing the channel.

31. A surgical access port comprising:
a device for retracting the edges of a surgical incision to form an opening into a patient's body cavity; and
a sealing sleeve attached to the device external to the body cavity, wherein the sealing sleeve comprises:
a flexible sleeve providing a channel from its open end distal to the retracting device through to the opening;
drawstrings connected to the flexible sleeve for sealing the channel; and an outer sleeve surrounding the flexible sleeve and forming a chamber therebetween, and an inlet port for inflating the chamber, whereby inflating the chamber compresses together a central portion of the flexible sleeve, thereby sealing the channel, and wherein the drawstrings attach to opposite sides of the central portion of the flexible sleeve.

32. A surgical access port comprising:
a device for retracting the edges of a surgical incision to form an opening into a patient's body cavity; and
a sealing sleeve attached to the device external to the body cavity, wherein the sealing sleeve comprises:
a flexible sleeve providing a channel from its open end distal to the retracting device through to the opening;
drawstrings connected to the flexible sleeve for sealing the channel; and a flap valve that connects to the open end of the flexible sleeve and extends into the channel, wherein the flap valve seals the channel when there is a positive pressure differential between the channel and the surroundings, and wherein the drawstrings attach to opposite ends of the flap valve to enhance the sealing ability of the flap valve.

33. A device for retracting edges of an incision in a surface to form an open channel, the device comprising:
an upper toroidal portion for positioning above the surface around the incision, the upper toroidal portion defining and enclosing an inflatable, sealed interior;
a lower portion insertable through the incision and orientable to underlie the surface beneath the incision; and a flexible, gas-tight tubular skirt having an upper end connected to the upper toroidal portion and a lower end connected to the lower portion, wherein during use the lower portion maintains the lower end in an open configuration, the upper toroidal portion, lower portion, and skirt defining an open channel extending through the incision, the channel having side-walls that are gas impermeable.

34. The device of claim 33, wherein the upper toroidal portion includes an inflation port for inflating the sealed interior.

35. The device of claim 33, wherein the lower portion is non-inflatable.

36. The device of claim 33, wherein the upper toroidal portion comprises two superimposed, inflatable collars.

37. A surgical access port comprising:
    the device of claim 33; and
    a flexible, gas-tight sleeve connected to the device and extending the channel away from the incision.

38. The access port of claim 37, wherein the sleeve is releasably connected to the device.

39. A surgical access port comprising:
    the device of claim 36; and
    a flexible, gas-tight sleeve connected to the device and extending the channel away from the incision, wherein the sleeve comprises a resilient ring configured to releasably attached to a groove formed between the two superimposed collars.

40. A method of retracting an incision into an opening and providing a channel through the incision, the channel having gas-impermeable sides and the method comprising:
    inserting a ring at one end of a gas-tight tubular skirt through the incision and orienting the ring to underlie and contact tissue surrounding the incision;
    orientating a toroidal upper portion at an opposite end of the gas-tight tubular skirt to overlie and contact tissue surrounding the incision; and
    expanding the toroidal upper portion, while maintaining the contact between the toroidal upper portion and the tissue surrounding the incision, to thereby draw the skirt outward from the incision, retract the incision into an opening, and provide the channel through the incision.

41. The method of claim 40, wherein the ring is non-inflatable.

42. A method of performing minimally invasive surgery, the method comprising:
    retracting an incision and providing a channel into the incision using the method of claim 40;
    releasably attaching a sleeve to the upper portion to extend the channel away from the incision, wherein the extended channel has gas-impermeable sides; and
    accessing an interior of a patient through the channel.

43. The method of claim 42, further comprising insufflating the interior of the patient.

* * * * *